United States Patent
Walker et al.

(10) Patent No.: US 10,952,873 B2
(45) Date of Patent: Mar. 23, 2021

(54) COMPACT MECHANICAL JOINT BALANCER

(71) Applicant: NEW YORK UNIVERSITY, New York, NY (US)

(72) Inventors: Peter Stanley Walker, New York, NY (US); Thomas Alfred Einhorn, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 16/938,178

(22) Filed: Jul. 24, 2020

(65) Prior Publication Data

US 2020/0352556 A1 Nov. 12, 2020

Related U.S. Application Data

(63) Continuation-in-part of application No. 16/257,490, filed on Jan. 25, 2019, now Pat. No. 10,758,375.

(60) Provisional application No. 62/621,852, filed on Jan. 25, 2018.

(51) Int. Cl.
| | |
|---|---|
| *A61F 2/46* | (2006.01) |
| *A61B 17/56* | (2006.01) |
| *A61B 17/02* | (2006.01) |
| *A61B 5/00* | (2006.01) |

(52) U.S. Cl.
CPC ............. *A61F 2/468* (2013.01); *A61B 5/458* (2013.01); *A61B 5/4585* (2013.01); *A61B 17/025* (2013.01); *A61B 17/56* (2013.01); *A61F 2/4657* (2013.01); *A61F 2/4684* (2013.01); *A61B 2017/0268* (2013.01); *A61B 2017/564* (2013.01); *A61F 2002/4658* (2013.01); *A61F 2002/4666* (2013.01); *A61F 2002/4668* (2013.01)

(58) Field of Classification Search
CPC .................. A61B 5/458; A61B 5/4585; A61B 2017/0268; A61B 17/56; A61B 17/66; A61B 2017/681; A61F 2/385; A61F 2/3872; A61F 2/46; A61F 2/4657; A61F 2002/4658; A61F 2002/4666; A61F 2002/4668; A61F 2/468
See application file for complete search history.

(56) References Cited

U.S. PATENT DOCUMENTS

| | | |
|---|---|---|
| 7,156,853 B2 | 1/2007 | Muratsu |
| 8,313,492 B2 | 11/2012 | Wong |
| 2014/0288563 A1 | 9/2014 | Claypool |
| 2015/0088140 A1 | 3/2015 | Toler |
| 2016/0135825 A1 | 5/2016 | Toler |

*Primary Examiner* — Larry E Waggle, Jr.
(74) *Attorney, Agent, or Firm* — Riverside Law LLP

(57) ABSTRACT

The present invention relates to devices and methods for balancing joints, including knee joints. The devices convert unequal forces at a joint to a rotation or displacement of a pointer or gauge. The devices are able to display the relative difference in force between the lateral and medial sides of a joint from flexion to extension. In certain aspects, the devices are useful for balancing the knee during total knee surgery. The devices can be inserted between the trial femoral and tibial components of the knee and measures whether one condyle experiences more force than the other.

14 Claims, 14 Drawing Sheets

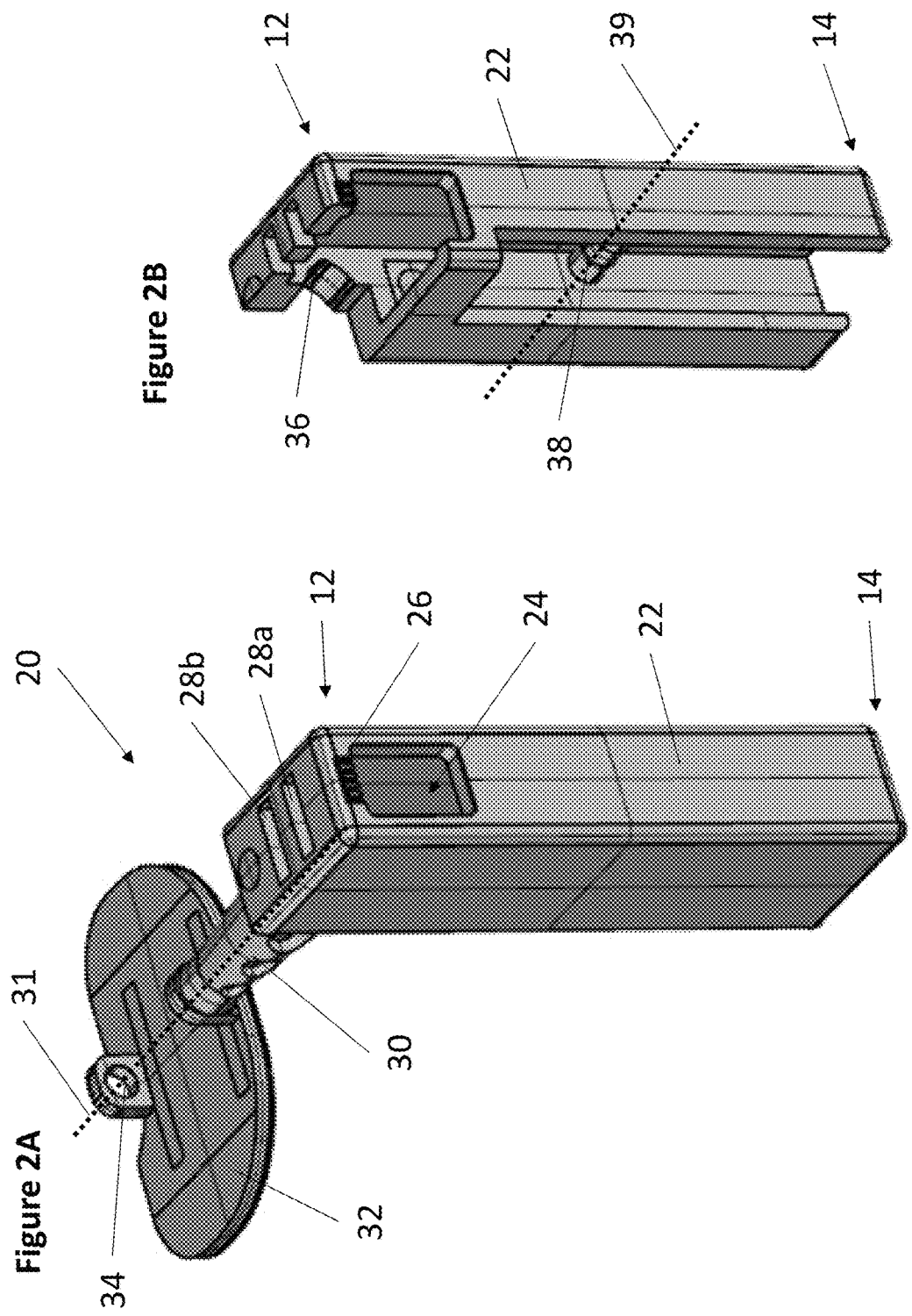

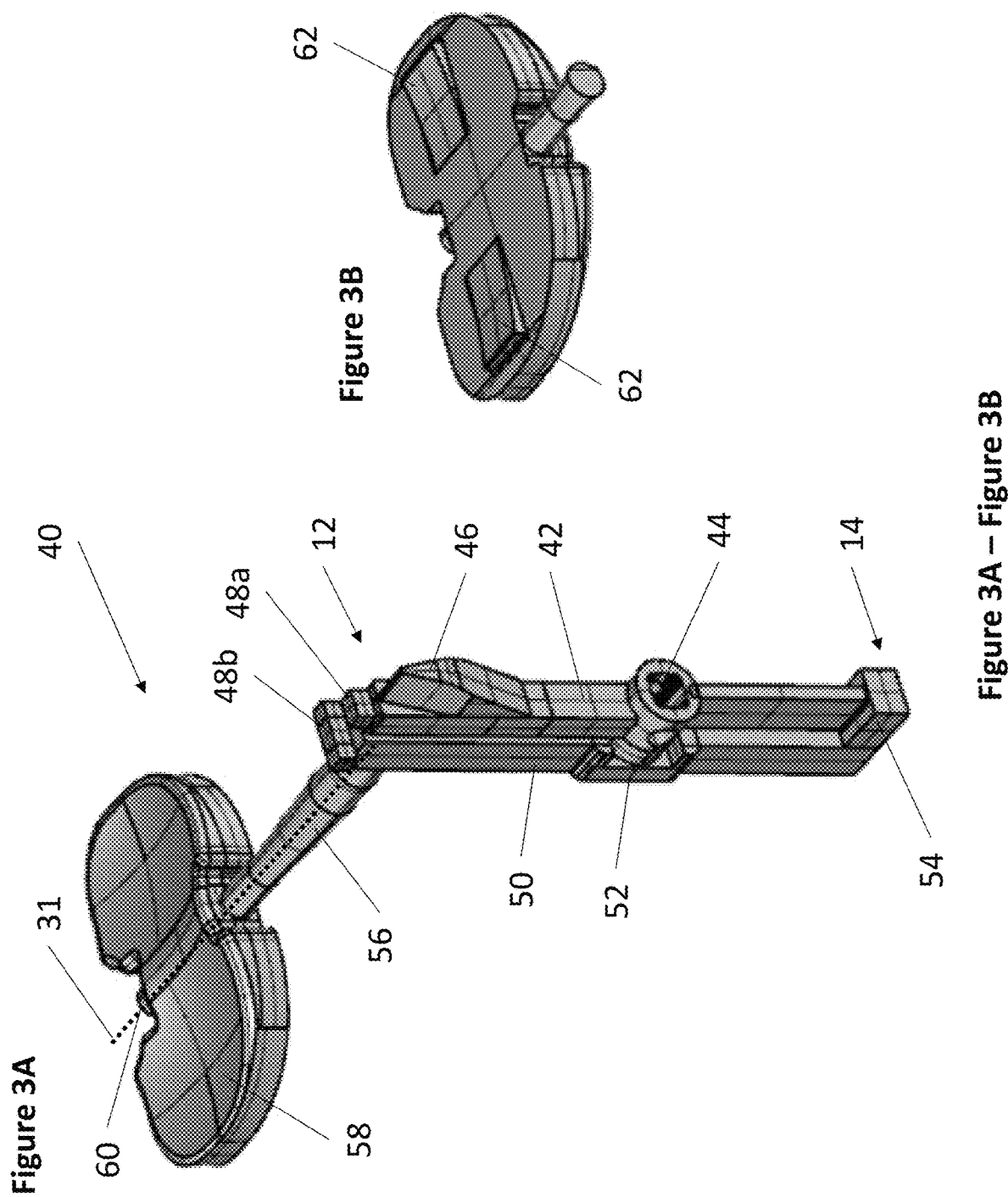

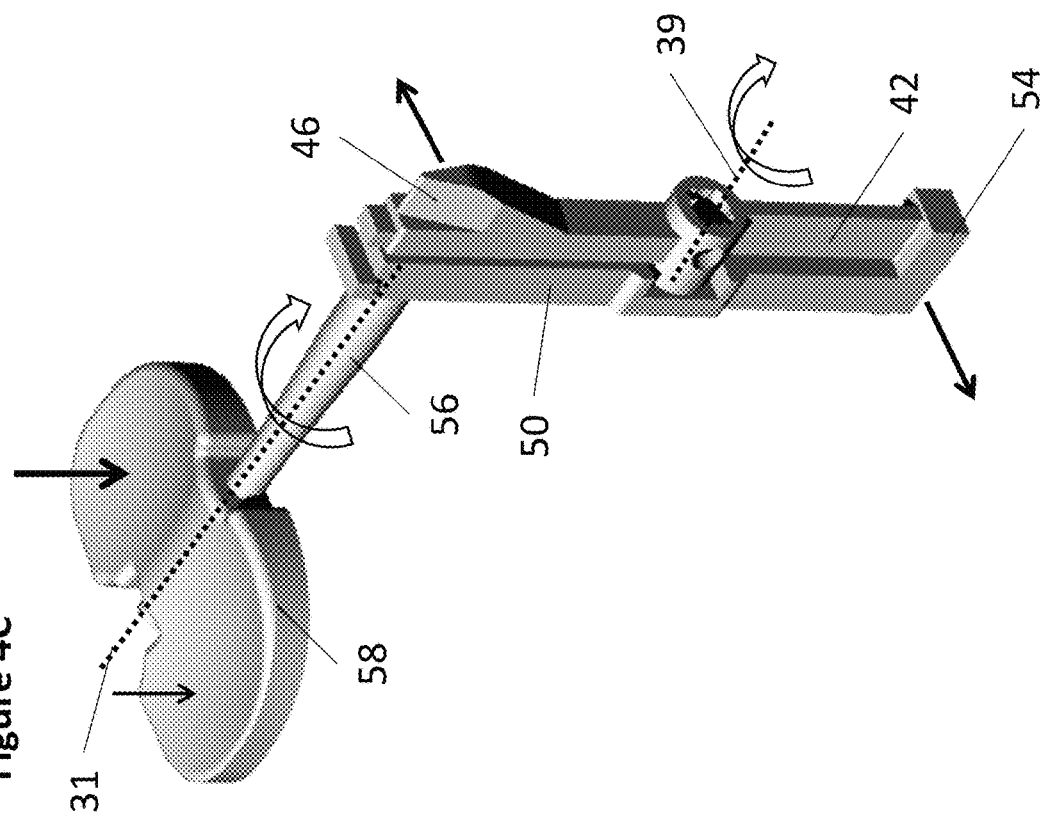
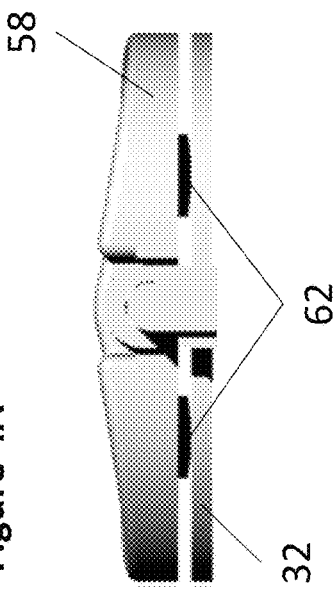
Figure 4A
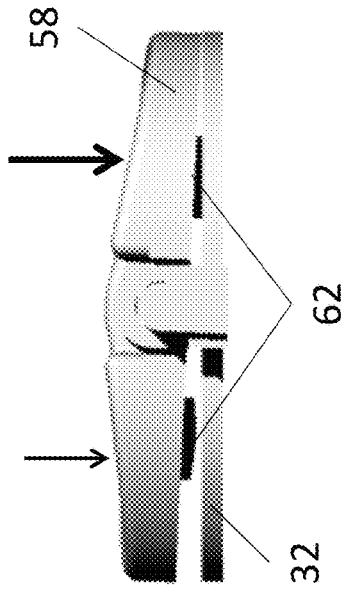
Figure 4B
Figure 4C
Figure 4A – Figure 4C

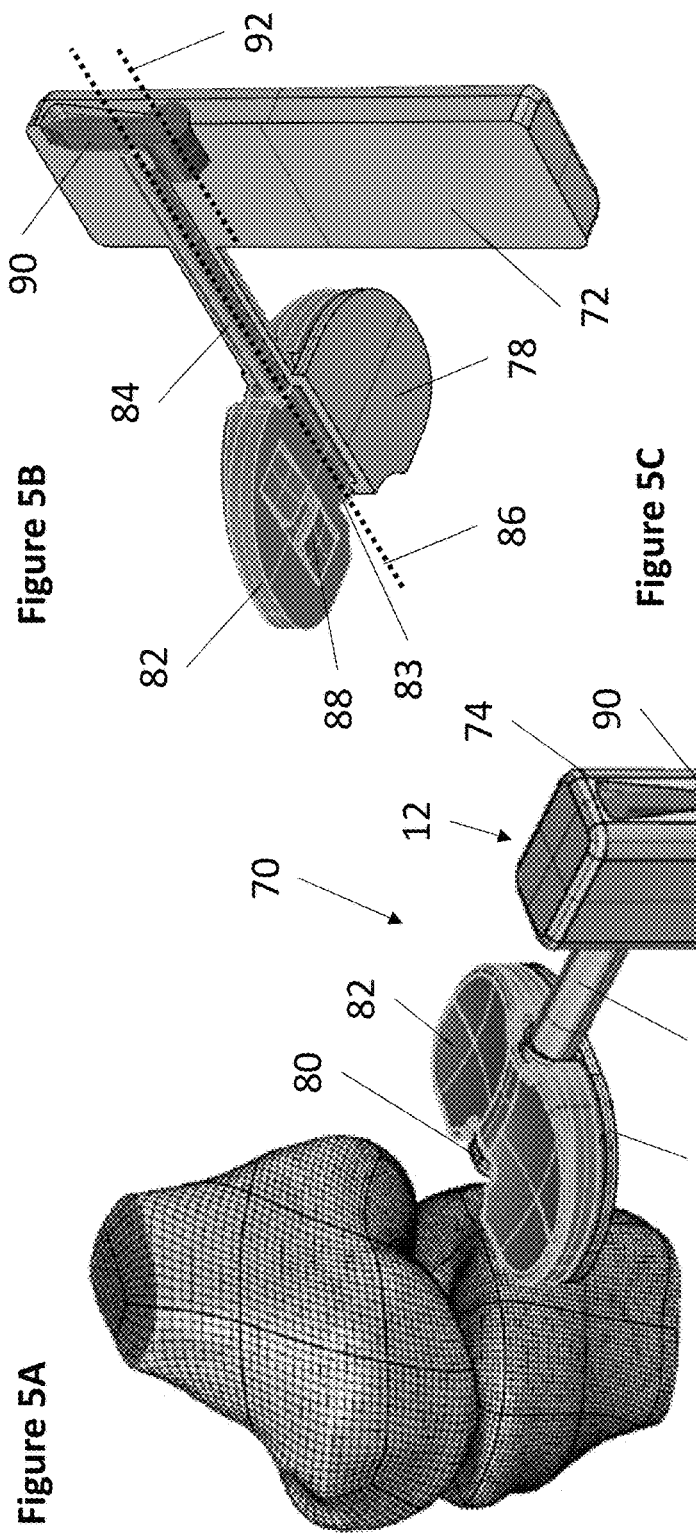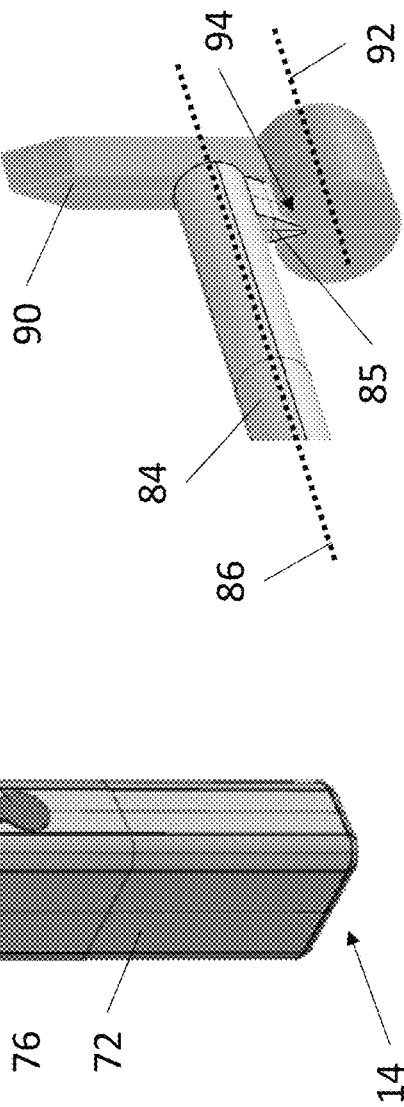

COMPACT MECHANICAL JOINT BALANCER

CROSS-REFERENCE TO RELATED APPLICATIONS

This application is a continuation-in-part of U.S. patent application Ser. No. 16/257,490, filed Jan. 25, 2019, now allowed, which claims priority to U.S. Provisional Patent Application No. 62/621,852, filed Jan. 25, 2018, the contents of which are each incorporated by reference herein in their entirety.

BACKGROUND OF THE INVENTION

In the normal intact knee, the relative position between the femur and the tibia is controlled by the shape of the bearing surfaces and by the 4 major ligaments crossing the knee; the anterior and posterior cruciates and the medial and lateral collaterals. As the knee is flexed and extended, the lengths of the ligaments and the shape of the bearing surfaces work in harmony to maintain stability, without excessive looseness or tightness. When the components of a total knee are inserted at surgery, it is important that the components are inserted accurately, and that the geometry of the components is sufficiently close to anatomic, so that the ligaments can still maintain the correct stability between the femur and the tibia.

In a typical surgical procedure, the bone cuts are made, then the trial components are inserted. At this stage, the knee is flexed and extended to determine whether the knee comes into extension without hyperextending, or having an extension lag. The thickness of the tibial component is adjusted if necessary. Then an assessment is made if the balancing is correct throughout flexion. A simple evaluation method is to remove the trials, introduce a spacer block between the cut surfaces of the femur and tibia with the knee in extension, and move the tibia into varus and valgus to assess the relative stiffnesses. This is repeated at 90 degrees flexion. If either the medial or lateral side of the knee is too tight, the tight ligaments are released.

Methods other than the spacer blocks can be used. One method is to use a distractor tool which inserts between the joint surfaces and equal expansion forces are applied separately to the lateral and medial condyles, equal distraction gaps being an indicator of balancing. More recently, an instrumented tibial trial has been introduced, which takes the place of the tibial trial component, which measures the lateral and medial contact forces throughout flexion and displays the forces on a computer screen.

Thus, there is a need in the art for improved mechanical devices and methods for balancing joints, including knee joints. The present invention meets this need.

SUMMARY OF THE INVENTION

The present invention relates to a joint balancer device, comprising: a handle having a gauge; a lower plate attached to the handle; and an upper plate aligned in parallel with the lower plate by a gap space, wherein the upper plate is displaceable relative to the lower plate; wherein the upper plate is connected by a mechanical link to the gauge, and wherein the mechanical link magnifies displacement of the upper plate such that the gauge displays the magnified displacement, wherein the mechanical link comprises: a first and a second long beam adjacently positioned within a hollow interior of the handle, each long beam having an anterior end as a pointer of the gauge; a first short beam extending from an interior of the lower plate in a lateral direction underneath a left side of the upper plate such that the first short beam attaches to a posterior end of the first long beam, wherein first short beam is further connected to the upper plate by a short vertical beam; a second short beam extending from an interior of the lower plate in a lateral direction underneath a right side of the upper plate such that the second short beam attaches to a posterior end of the second long beam, wherein the second short beam is further connected to the upper plate by a short vertical beam; a first fulcrum beam extending from an interior of the lower plate in a lateral direction underneath a left side of the upper plate, the first fulcrum beam positioned anterior to the first short beam such that the first fulcrum beam attaches to the first long beam at a position anterior to the first short beam; and a second fulcrum beam extending from an interior of the lower plate in a lateral direction underneath a right side of the upper plate, the second fulcrum beam positioned anterior to the second short beam such that the second fulcrum beam attaches to the second long beam at a position anterior to the second short beam.

In one embodiment, an inferior displacement of a side of the upper plate inferiorly displaces the respective short beam underneath the side of the upper plate, such that the respective connected long beam is actuated about the respective fulcrum beam to shift the pointer of the gauge in a superior direction. In one embodiment, the upper plate comprises flexible membranes above the first and second short beams.

In one embodiment, the upper plate has an upper surface contoured to fit a femur's condyles or a trial femoral component of a total knee replacement, and the lower plate has a lower surface contoured to fit a resected surface of a tibia in a total knee replacement.

In one embodiment, the upper plate and the lower plate are separated by a substantially parallel distance between about 1 and 3 mm. In one embodiment, the upper plate is cantilevered over the lower plate by the distance. In one embodiment, the distance is maintained in a neutral state by one or more springs positioned between the upper plate and the lower plate, the one or more springs selected from the group consisting of: coil springs, conical springs, wave springs, and leaf springs.

In one embodiment, the gauge includes a scale having at least one of force units, distance units, angle degrees, or unitless markings. In one embodiment, the device is configured to measure a relative difference in force between a lateral side and a medial side of a joint.

In another aspect, the present invention relates to a method of balancing a joint, comprising the steps of: providing the balancer device of the present invention; inserting the balancer device into a joint in need of balancing such that the upper and lower plates rest against opposing surfaces of the joint; flexing the joint through at least part of its full range of motion; recording the magnitudes of displacement or force between left and right sides of the joint indicated by the gauge throughout the flexing of the joint; removing the balancer device from the joint; and modifying the balance of the joint based on the magnitudes of displacement or force between left and right sides of the joint.

In one embodiment, the joint is a knee joint or an elbow joint. In one embodiment, the opposing joint surfaces are opposing bone surfaces, opposing implant surfaces, or combinations thereof. In one embodiment, the balance of the joint is modified by trimming the opposing surfaces, raising the opposing surfaces, adjusting a spacer component between the opposing surfaces, or combinations thereof. In one embodiment, contact forces are increased between the joint and the balancer device by adding one or more additional spacer plates to the upper plate and/or lower plate.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

FIG. 2A and FIG. 2B depict perspective views of the handle component of an exemplary balancer device. FIG. 2A depicts the handle alone. FIG. 2B depicts a partial cutaway view of the handle.

FIG. 3A and FIG. 3B depict perspective views of the balancer component of an exemplary balancer device comprising a condyle and a mechanical linkage. FIG. 3A depicts the balancer component alone. FIG. 3B depicts a partial view of the bottom surface of the balancer component.

FIG. 4A through FIG. 4C depict various views of the balancer component of an exemplary balancer device as it receives a load. FIG. 4A depicts a frontal view of the balancer plate and handle plate at rest. FIG. 4B depicts a frontal view of the balancer plate and handle plate receiving a load on the right condyle. FIG. 4C depicts a perspective view of the balancer component receiving a load on the right condyle, causing the pointer or gauge to provide a reading to the right.

FIG. 5A through FIG. 5C depict various views of another exemplary balancer device. FIG. 5A depicts the balancer device near a knee joint. FIG. 5B depicts a partially cutaway view of the underside of the balancer device. FIG. 5C depicts the balancer component and pointer or gauge in isolation.

DETAILED DESCRIPTION

Figure 1:
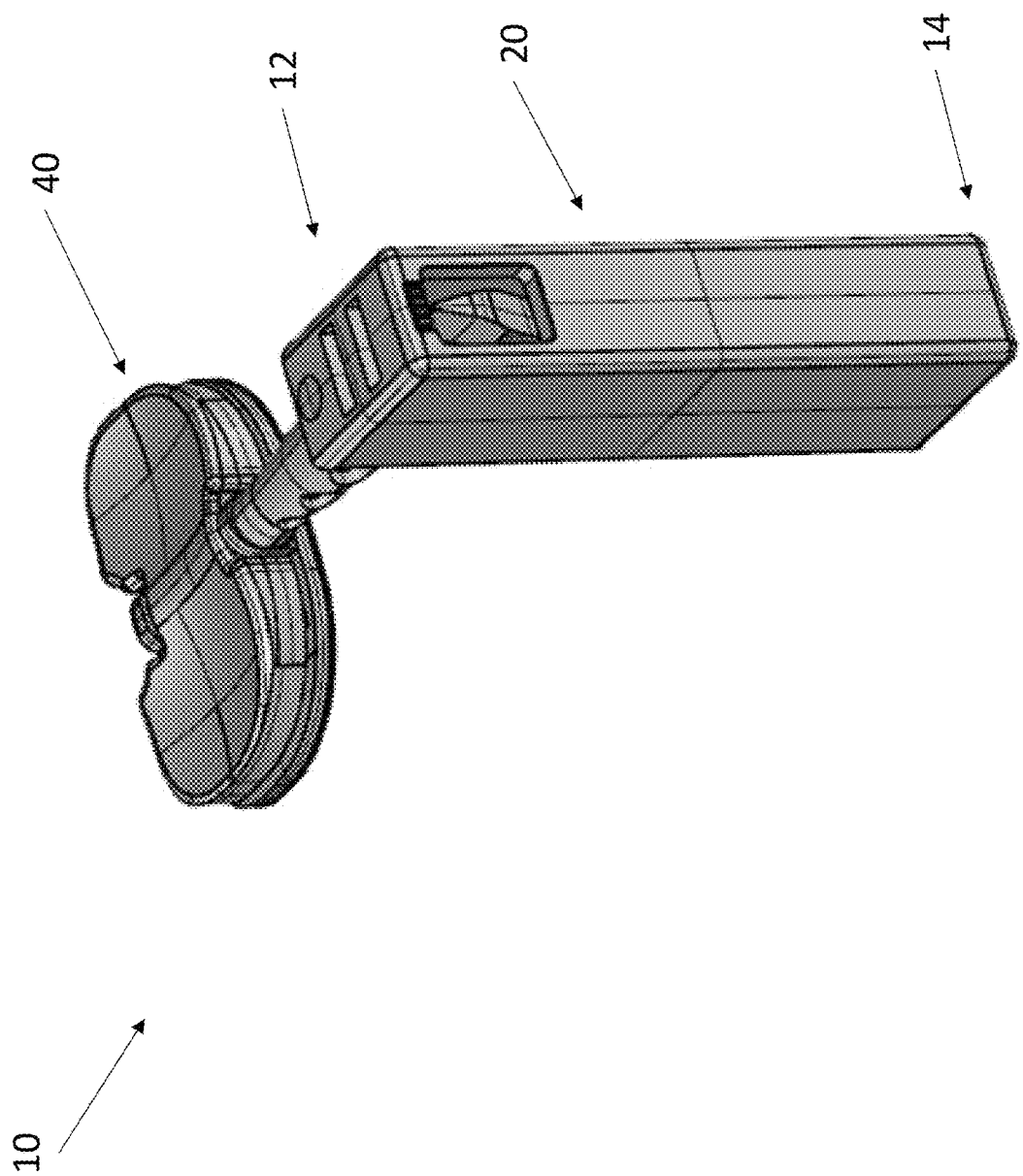
FIG. 1 depicts a perspective view of an exemplary balancer device.

The present invention relates to devices and methods for balancing joints, including knee joints. The devices convert unequal forces at a joint to a rotation or displacement of a pointer or gauge. The devices are able to display the relative difference in force between the lateral and medial sides of a joint from flexion to extension. In certain aspects, the devices are useful for balancing the knee during total knee surgery. The devices can be inserted between the trial femoral and tibial components of the knee and measures whether one condyle experiences more force than the other.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

The terms "proximal," "distal," "anterior," "posterior," "medial," "lateral," "superior," and "inferior" are defined by their standard usage indicating a directional term of reference. For example, "proximal" refers to an upper location from a point of reference, while "distal" refers to a lower location from a point of reference. In another example, "anterior" refers to the front of a body or structure, while "posterior" refers to the rear of a body or structure. In another example, "medial" refers to the direction towards the midline of a body or structure, and "lateral" refers to the direction away from the midline of a body or structure. In some examples, "lateral" or "laterally" may refer to any sideways direction. In another example, "superior" refers to the top of a body or structure, while "inferior" refers to the bottom of a body or structure. It should be understood, however, that the directional term of reference may be interpreted within the context of a specific body or structure, such that a directional term referring to a location in the context of the reference body or structure may remain consistent as the orientation of the body or structure changes.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

Balancer Device

Referring now to FIG. 1, an exemplary balancer device 10 is depicted. Balancer device 10 has a superior end 12, an inferior end 14, and comprises a balancer plate 40 partially encased within a handle component 20.

Referring now to FIG. 2A and FIG. 2B, handle 20 of an exemplary balancer device 10 is depicted in isolation. Handle 20 comprises housing 22, axle casing 30, and plate 32. Housing 22 comprises a substantially hollow construction having a superior end 12 and an inferior end 14. Housing 22 comprises a window 24 and a scale 26 positioned near its superior end 12. Scale 26 provides a graded measure of any suitable unit adjacent to window 24. For example, scale 26 can include at least one of force units, distance units, angle degrees, or unitless markings. Housing 22 further comprises a first tab slot 28a and a second tab slot 28b positioned on the top of its superior end 12. Pin 38, aligned along axis 39, is positioned within the hollow interior of housing 22 and projects from the anterior surface of housing 22 in an anterior to posterior direction.

Axle casing 30 extends posteriorly from housing 22 and connects at its posterior end to plate 32. Axle casing 30 comprises a lumen extending from the hollow interior of housing 22 (at axle opening 36) to an open end adjacent to plate 32. Plate 32 can have any suitable shape, such as a substantially planar shape sized to fit within a joint space between two connected bones to fit on a lower surface within a joint, such as on a resected tibial surface in the knee. Plate 32 has an upper surface that interfaces with balancer plate 40. In some embodiments, plate 32 has a flat upper surface. In other embodiments, plate 32 has a curved upper surface. In some embodiments, plate 32 has a flat lower surface. In other embodiments, plate 32 has a contoured periphery or lower surface having the shape of a joint space, such as the resected proximal surface of a tibia in a total knee replacement. Plate 32 includes axle slot 34 positioned opposite from the open end of axle casing 30 and aligned with the lumen of axle casing 30.

Referring now to FIG. 3A and FIG. 3B, balancer plate 40 of an exemplary balancer device 10 is depicted in isolation viewed from an anterior direction, alternately called the underside. Balancer plate 40 comprises first beam 42, second beam 50, axle 56, and plate 58. First beam 42 and second beam 50 each comprises an elongate shape having a superior end 12 and an inferior end 14. First beam 42 comprises pin bore 44 positioned between its superior end 12 and inferior end 14. Pin bore 44 is sized to fit around pin 38 such that first beam 42 is at least partially rotatable about pin 38. First beam 42 further comprises pointer or gauge 46 positioned near its superior end 12 and first tab 48a positioned on the top end of its superior end 12. Pointer or gauge 46 is visible through window 24 adjacent to scale 26, such that the position of pointer or gauge 46 indicates the instant numerical measure as measured by balancer device 10. First tab 48a fits within first tab slot 28a and limits the movement of first beam 42 to the boundaries of first tab slot 28a.

First beam 42 is attached to second beam 50 at their inferior ends 14 by extension 54. In some embodiments the inferior half of first beam 42 below pin bore 44 is at least partially flexible. A flexible inferior half of first beam 42 below pin bore 44 compensates for the different centers of rotation of second beam 50 and first beam 42. The flexible portion also acts as a spring to center pointer or gauge 46 when no load is present in device 10. In some embodiments, the attachment between the inferior end of first beam 42 and second beam 50 is a rigid attachment, such as by an adhesive, a welding, or by forming first beam 42 and second beam 50 as a single continuous piece. In other embodiments, the attachment between the inferior end of first beam 42 and second beam 50 is a separable attachment, such as by slotting the inferior end 14 of first beam 42 into an opening in extension 54. Second beam 50 is thereby positioned parallel and adjacent to first beam 42, such that both can fit within the hollow interior of housing 22. Second beam 50 comprises indent 52 between its superior end 12 and inferior end 14. Indent 52 provides freedom for second beam 50 to travel around pin bore 44. Second beam 50 comprises second tab 48b positioned on the top end of its superior end 12. Second tab 48b fits within second tab slot 28b and limits the movement of second beam 50 to the boundaries of second tab slot 28b.

Axle 56 extends posteriorly from the superior end 12 of second beam 50 along axis 31 and connects at its posterior end to plate 58. Plate 58 comprises axle tip 60 positioned opposite from axle 56 and aligned with axis 31. Plate 58 can have any suitable shape, such as a substantially planar shape sized to fit within a joint space between two connected bones. In some embodiments, plate 58 has a flat upper surface. In other embodiments, plate 58 has a contoured or concave upper surface having a shape that fits in a joint space, such as a shape that fits against the condyles of a trial femoral component of a total knee replacement. As described elsewhere herein, the bottom surface of plate 58 can be contoured to fit the upper surface of plate 32. For example, a plate 58 having a flat lower surface fits with a plate 32 having a flat upper surface, and a plate 58 having a curved lower surface fits with a plate 32 having a curved upper surface.

The lower surface of plate 58 has at least two springs 62 positioned opposite from each other to the left and to the right of axle 56. Springs 62 can be any suitable spring, such as a coil spring, a conical spring, a wave spring, a leaf spring, and the like. The lower surface of plate 58 is in parallel alignment with the upper surface of plate 32 at rest, with springs 62 maintaining a constant height difference between both plates at rest, as well as restoring parallel alignment to both plates after displacement of plate 58, thereby functioning as a centering mechanism to zero pointer or gauge 46 of device 10. Plate 58 and plate 32 can be separated by any suitable height, such as a height between about 1 and 5 mm or between about 1 and 3 mm. In some embodiments, the height between plate 58 and plate 32 is 2.5 mm.

Balancer device 10 uses balancer plate 40 and handle 20 to provide a reading of the relative difference in force between the lateral and medial sides of a joint by translating displacement of plate 58 into a proportional movement of pointer or gauge 46. The displacement can be an angular displacement, a rotation, or a vertical displacement. Referring now to FIG. 4A through FIG. 4C, the operational relationship between balancer plate 40 and handle 20 is depicted. It should be understood that while joints attached to a body as a point of reference can have medial and lateral sides, for the sake of example a hypothetical joint being measured by balancer device 10 has a left and a right side as depicted in FIG. 4B and FIG. 4C. In FIG. 4A, balancer device 10 is shown at rest. Plate 58 of balancer plate 40 and plate 32 of handle 20 are held in parallel alignment by springs 62. In FIG. 4B, an imbalance in a hypothetical joint leads to a relative difference in force that is greater on the right side, which depresses right spring 62 on plate 58. In FIG. 4C, the greater force on the right side of plate 58 causes axle 56 to rotate about axis 31 in a clockwise direction, such as up to 5 degrees or up to 2.5 degrees. Second beam 50, being connected at its superior end to axle 56, pivots in a clockwise direction about its connection with axle 56, causing its inferior end to move laterally to the left. As one side of balancer plate 40 moves down and the opposite side moves up, the ligament tension will reduce and increase respectively. Hence, this also contributes to the mechanism where balancer plate 40 reaches an equilibrium angle of rotation. The leftward movement of the inferior end of second beam 50 also shifts the inferior end of first beam 42 in a leftward direction due to the connection between second beam 50 and first beam 42 at extension 54. First beam 42, being rotatably connected to pin 38, thereby pivots in a clockwise direction about axis 39, causing the superior end of first beam 42, along with pointer or gauge 46 to move laterally to the right. In various embodiments, the position of axis 39 can be raised or lowered to adjust the magnification of movement between the inferior end 14 of second beam 50 and pointer or gauge 46.

In summary, a relative difference in force between the left and right side of a joint exerts a greater load on a respective side of plate 58. The greater load displaces plate 58, such as an angular displacement, a rotation, or a vertical displacement, which rotates axle 56. The rotation of axle 56 and the mechanically linked movement of second beam 50 and first beam 42 is translated to a shift in the position of pointer or gauge 46 to the left or to the right, whereupon pointer or gauge 46 points to a unit on scale 26 of housing 22 to indicate the relative difference in force in the joint on the side with the greater load. Movement in pointer or gauge 46 is thereby representative of a magnified magnitude of the movement of plate 58.

Referring now to FIG. 5A through FIG. 5C, an exemplary balancer device 70 is depicted. Balancer device 70 comprises a housing 72 with a superior end 12 and an inferior end 14. Housing 72 comprises a window 74 near its superior end 12 sized to fit a pointer or gauge 90. Housing 72 may further comprise a scale positioned near its superior end 12 that provides a graded measure of any suitable unit adjacent to window 74 (not pictured). For example, the scale can include at least one of force units, distance units, angle degrees, or unitless markings. Axle casing 76 extends posteriorly from the superior end 12 of housing 72 and connects at its posterior end to plate 78. Axle casing 76 comprises a lumen extending from housing 72 to an open end adjacent to plate 78. Plate 78 can have any suitable shape, such as a substantially planar shape sized to fit within a joint space between two connected bones. Plate 78 has an upper surface that interfaces with the lower surface of balancer plate 82, such that a flat upper surface of plate 78 fits with a flat lower surface of balancer plate 82, and a curved upper surface of plate 78 fits with a curved lower surface of balancer plate 82. In some embodiments, plate 78 has a flat lower surface. In other embodiments, plate 78 has a contoured lower surface having a shape that fits in a joint space, such as a shape that fits with the condyles of a tibia in a knee joint. Plate 78 includes axle slot 80 positioned opposite from the open end of axle casing 76 and aligned with the lumen of axle casing 76.

Balancer plate 82 rests on the upper surface of plate 78 and is connected to the posterior end of axle 84. Axle 84, aligned along axis 86, extends anteriorly through the lumen of axle casing 76 into housing 72. Balancer plate 82 comprises axle tip 83 positioned opposite from axle 84 and aligned with axis 86. Balancer plate 82 can have any suitable shape, such as a substantially planar shape sized to fit within a joint space between two connected bones. In some embodiments, balancer plate 82 has a flat upper surface. In other embodiments, balancer plate 82 has a contoured or concave upper surface having a shape that fits in a joint space, such as a shape that fits with the condyles of a femur in a knee joint. The lower surface of balancer plate 82 has at least two springs 88 positioned opposite from each other to the left and to the right of axle 84. Springs 88 can be any suitable spring, such as a coil spring, a conical spring, a wave spring, a leaf spring, and the like. The lower surface of balancer plate 82 is in parallel alignment with the upper surface of plate 78 at rest, with springs 88 maintaining a constant height difference between both plates at rest. Balancer plate 82 and plate 78 can be separated by any suitable height, such as a height between about 1 and 5 mm or between about 1 and 3 mm. In some embodiments, the height between balancer plate 82 and plate 78 is 2.5 mm.

Axle 84 comprises tab 85 at its anterior end that seats within notch 94 of pointer or gauge 90. Balancer device 70 thereby is able to provide a reading of the relative difference in force between the lateral and medial sides of a joint by translating displacement of balancer plate 82 into a proportional movement of pointer or gauge 90. The displacement can be an angular displacement, a rotation, or a vertical displacement.

While joints attached to a body as a point of reference can have medial and lateral sides, for the sake of describing the function of balancer device 70 in an example, a hypothetical joint being measured by balancer device 70 has a left and a right side relative to the orientation of the device in FIG. 5A and FIG. 5B. An imbalance in a hypothetical joint leads to a relative difference in force that is greater on the right side, which depresses the right spring 88 of plate 85 and causes axle 84 to rotate in a clockwise direction along axis 86, such as up to 5 degrees or up to 2.5 degrees. The rotation of axle 84 in a clockwise direction pivots tab 85 in a clockwise direction to the left, which pushes notch 94 in the left direction, causing pointer or gauge 90 to pivot along axis 92 to the left. In this embodiment, pointer or gauge 90 would point to a measure of magnitude, whereupon a user taking care to reverse the orientation may assign the greater load to the correct side of imbalance (e.g. the pointer or gauge 90 pointing to the left indicates a greater load on the right side of balancer plate 82). In some embodiments, pointer or gauge 90 points towards inferior end 14, whereupon tab 85 pushing notch 94 in the left direction causes pointer or gauge 90 to pivot along axis 92 to the right, in the same direction as the greater load on the right side of balancer plate 82 (not pictured). In every embodiment, movement in pointer or gauge 90 is thereby representative of a magnified magnitude of the movement of balancer plate 82.

Figure 6:
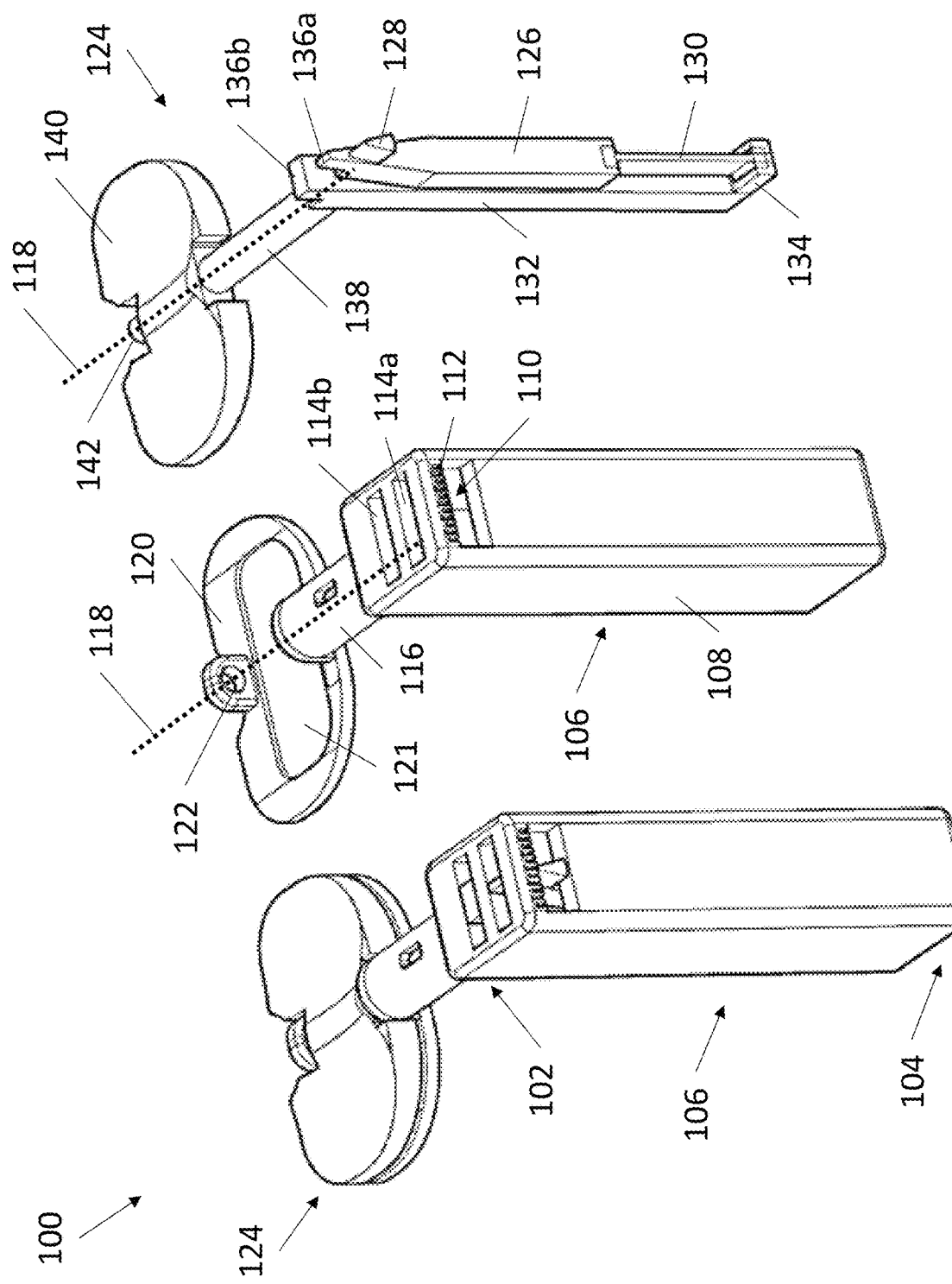
FIG. 6 depicts perspective views of another exemplary balancer device. The balancer device (left) includes a handle (middle) and a balancer component (right).

Referring now to FIG. 6, an exemplary balancer device 100 is depicted. Balancer device 100 has a superior end 102, an inferior end 104, and comprises a balancer component 124 partially encased within a handle component 106. Handle 106 comprises housing 108, axle casing 116, and plate 120. Housing 108 comprises a substantially hollow construction with a window 110 and a scale 112 positioned near its superior end 102. Scale 112 provides a graded measure of any suitable unit adjacent to window 110. For example, scale 112 can include at least one of force units, distance units, angle degrees, or unitless markings. Housing 108 further comprises a first tab slot 114a and a second tab slot 114b positioned on the top of its superior end 102. Visible in FIG. 7 (middle and right), housing 108 further comprises opposing studs 146 having a gap space in-between.

Axle casing 116 extends posteriorly from housing 108 and connects at its posterior end to plate 120. Axle casing 116 comprises a lumen extending from the hollow interior of housing 108 to an open end adjacent to plate 120. Plate 120 can have any suitable shape, such as a substantially planar shape sized to fit within a joint space between two connected bones. Plate 120 has an upper surface that interfaces with balancer 124. In some embodiments, plate 120 has a flat upper surface. In other embodiments, the upper surface of plate 120 comprises recess 121. In some embodiments, plate 120 has a flat lower surface. In other embodiments, plate 120 has a contoured periphery or lower surface having the shape of a joint space, such as the resected proximal surface of a tibia in a total knee replacement. Plate 120 includes axle slot 122 positioned opposite from the open end of axle casing 116 and aligned with the lumen of axle casing 116.

Figure 7:
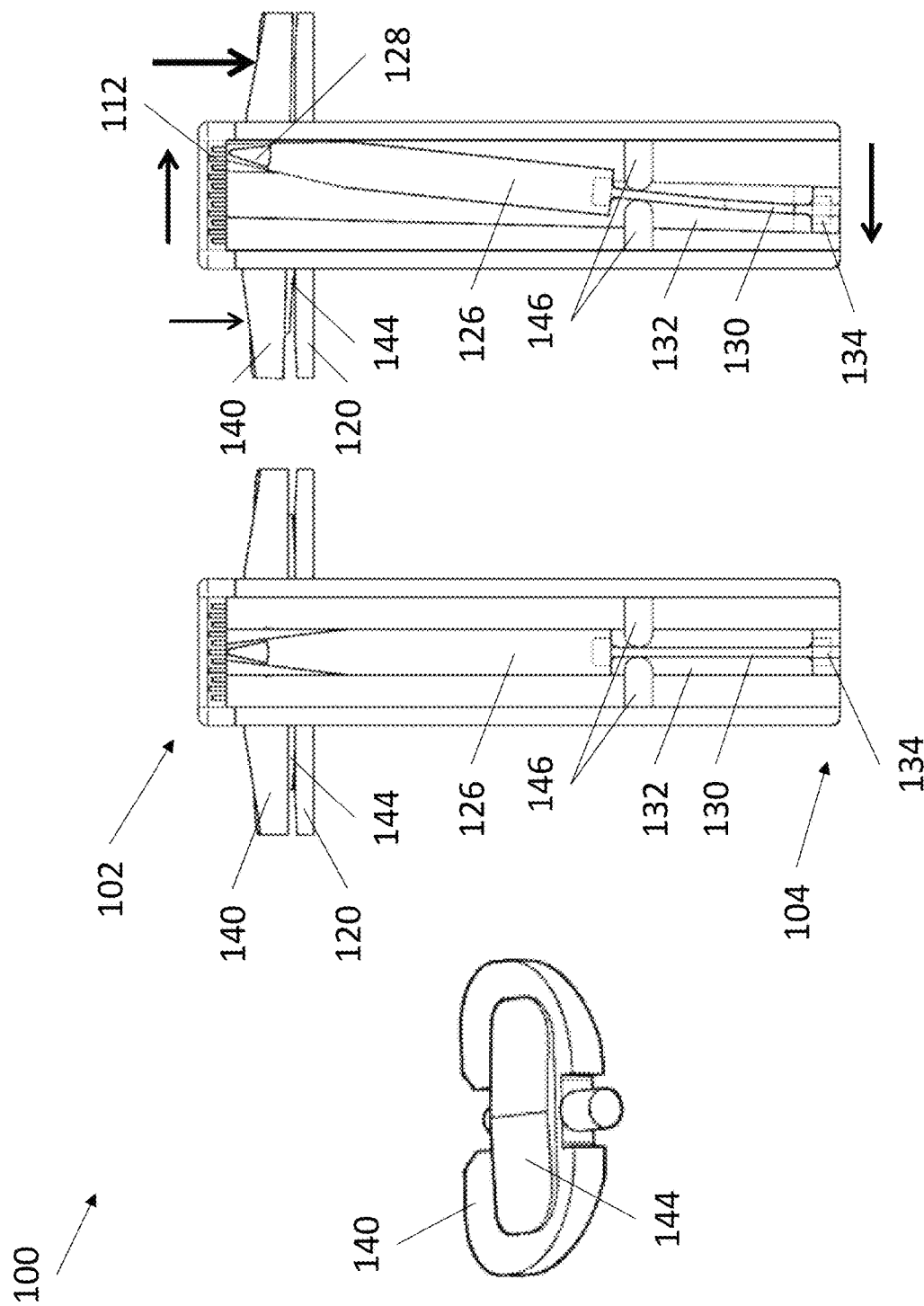
FIG. 7 depicts certain views of the balancer device in FIG. 6, including the underside of the plate of a condylar component (left), a partial cutaway view of the device under no load (middle), and a partial cutaway view of the device under load (right).

Balancer 124 comprises first beam 126, second beam 132, axle 138, and plate 140. First beam 126 and second beam 132 each comprises an elongate shape. First beam 126 comprises pointer or gauge 128 and first tab 136a at superior end 102 and a flexible beam 130 at inferior end 104, wherein first tab 136a is sized to fit within first tab slot 114a. Flexible beam 130, similar to the flexible inferior half of first beam 42, magnifies the movement of pointer or gauge 128 and acts as a spring to center pointer or gauge 128 when no load is present in device 100. Pointer or gauge 128 is visible through window 110 adjacent to scale 112, such that the position of pointer or gauge 128 indicates the instant numerical measure as measured by balancer device 100. Flexible beam 130 has a width that is smaller than first beam 126, such that flexible beam 130 fits within the gap space between opposing studs 146 in the interior of housing 108 (FIG. 7, middle and right). In some embodiments, studs 146 are positioned from about one third of the height of handle 106. In various embodiments, the position of studs 146 can be raised or lowered within housing 108 to adjust the magnitude of movement between the inferior end 104 of second beam 132 and pointer or gauge 128. Second beam 132 comprises second tab 136b at superior end 102 and extension 134 at inferior end 104, wherein second tab 136b is sized to fit within second tab slot 114b. First beam 126 is attached by way of flexible beam 130 to second beam 132 at their inferior ends 104 by extension 134. In some embodiments, the attachment at extension 134 is a rigid attachment, such as by an adhesive, a welding, or by forming first beam 126 and second beam 132 as a single continuous piece. In other embodiments, the attachment at extension 134 is a separable attachment, such as by slotting inferior end 104 of flexible beam 130 into an opening in extension 134. Second beam 132 is thereby positioned parallel and adjacent to first beam 126, such that both can fit within the hollow interior of housing 108.

Axle 138 extends posteriorly from superior end 102 of second beam 132 along axis 118 and connects at its posterior end to plate 140. Plate 140 comprises axle tip 142 positioned opposite from axle 138 and aligned with axis 118. Plate 140 can have any suitable shape, such as a substantially planar shape sized to fit within a joint space between two connected bones. In some embodiments, plate 140 has a flat upper surface. In other embodiments, plate 140 has a contoured or concave upper surface having a shape that fits in a joint space, such as a shape that fits against the condyles of a trial femoral component of a total knee replacement. As described elsewhere herein, the bottom surface of plate 140 can be contoured to fit the upper surface of plate 120. For example, a plate 140 having a flat lower surface can fit with a plate 120 having a flat upper surface. In some embodiments the lower surface of plate 140 can include support 144 shown in FIG. 7 (left) to increase the stiffness of plate 140 under load; support 144 can fit within a recess 121 in the upper surface of plate 120. Support 144 comprises two downward sloping surfaces meeting at a middle edge, wherein the height of the edge combined with the depth of recess 121 define the height of parallel alignment between the lower surface of plate 140 and the upper surface of plate 120 at rest. Plate 140 and plate 120 can be separated by any suitable height, such as a height between about 1 and 5 mm or between about 1 and 3 mm. In some embodiments, the height between plate 140 and plate 120 is 2.5 mm.

Similar to the embodiments described elsewhere herein, balancer device 100 uses balancer 124 and handle 106 to provide a reading of the relative difference in force between the lateral and medial sides of a joint by translating displacement of plate 140 into a proportional movement of pointer or gauge 128. The displacement can be an angular displacement, a rotation, or a vertical displacement. Referring now to FIG. 7 (middle and right), the operational relationship between balancer 124 and handle 106 is depicted. It should be understood that while joints attached to a body as a point of reference can have medial and lateral sides, for the sake of example a hypothetical joint being measured by balancer device 100 has a left and a right side as depicted in FIG. 7 (middle and right). In FIG. 7 (middle), balancer device 100 is shown at rest. Plate 140 of balancer 124 and plate 120 of handle 106 are held in parallel alignment by the edge of support 144 resting at the bottom of recess 121. In FIG. 7 (right), an imbalance in a hypothetical joint leads to a relative difference in force that is greater on the right side, which depresses the right side of plate 140. The greater force on the right side of plate 140 causes plate 140 to tilt and rotates axle 138 about axis 118 in a clockwise direction, such as up to 5 degrees or up to 2.5 degrees. Second beam 132, being connected at its superior end 102 to axle 138, pivots in a clockwise direction about its connection with axle 138, causing its inferior end 104 to move laterally to the left. The leftward movement of the inferior end 104 of second beam 132 also shifts the inferior end of flexible beam 130 in a leftward direction due to the connection between second beam 132 and flexible beam 130 at extension 134. The movement of flexible beam 130, being constrained by studs 146, thereby pivots the superior end 102 of first beam 126 in a clockwise direction, causing pointer or gauge 128 to move laterally to the right. Movement in pointer or gauge 128 is thereby representative of a magnified magnitude of the movement of plate 140.

Figure 8:
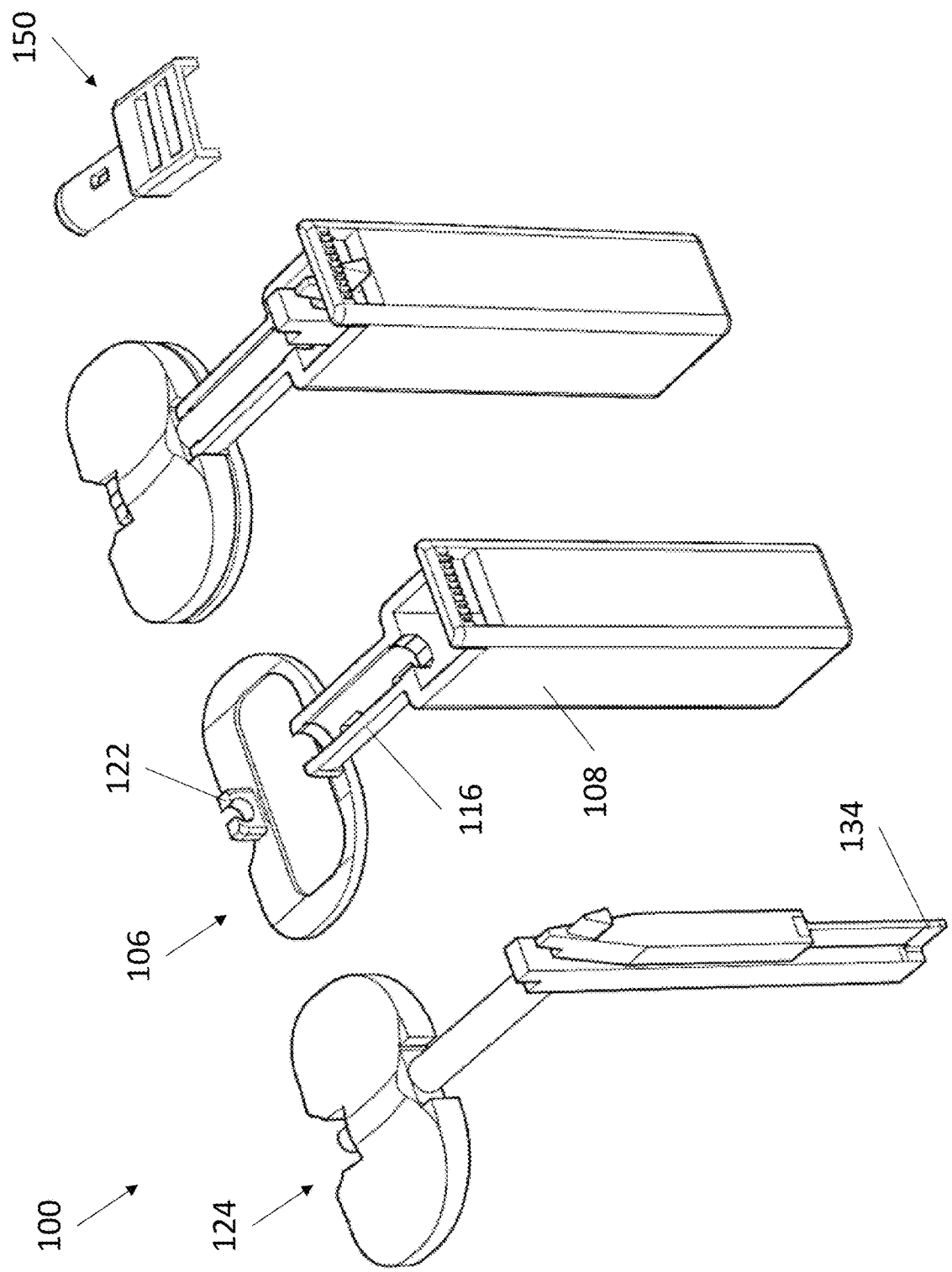
FIG. 8 depicts perspective views of the balancer device in FIG. 6 as separable components that can be snap fit together. The separable components include a balancer component (far left) and a handle component (middle left) that can be combined to form the balancer device (middle right), and optionally a cap (far right).

In some embodiments, handle 106 and balancer 124 can be snap fit together to assemble balancer device 100, as depicted in FIG. 8. For example, extension 134 (FIG. 8, far left) can be sized to have a width substantially equal to flexible beam 130, such that extension 134 and flexible beam 130 can both slide in between the gap space between opposing studs 146. Handle 106 (FIG. 8, middle left) can have an axle slot 122, an axle casing 116, and a housing 108 having open superior ends 102, enabling balancer 124 to be inserted into handle 106 from a superior direction (FIG. 8, middle right). In some embodiments, balancer device 100 can further include cap 150 (FIG. 8, far right) to close off the superior ends 102 of axle casing 116 and housing 108.

Figure 9:
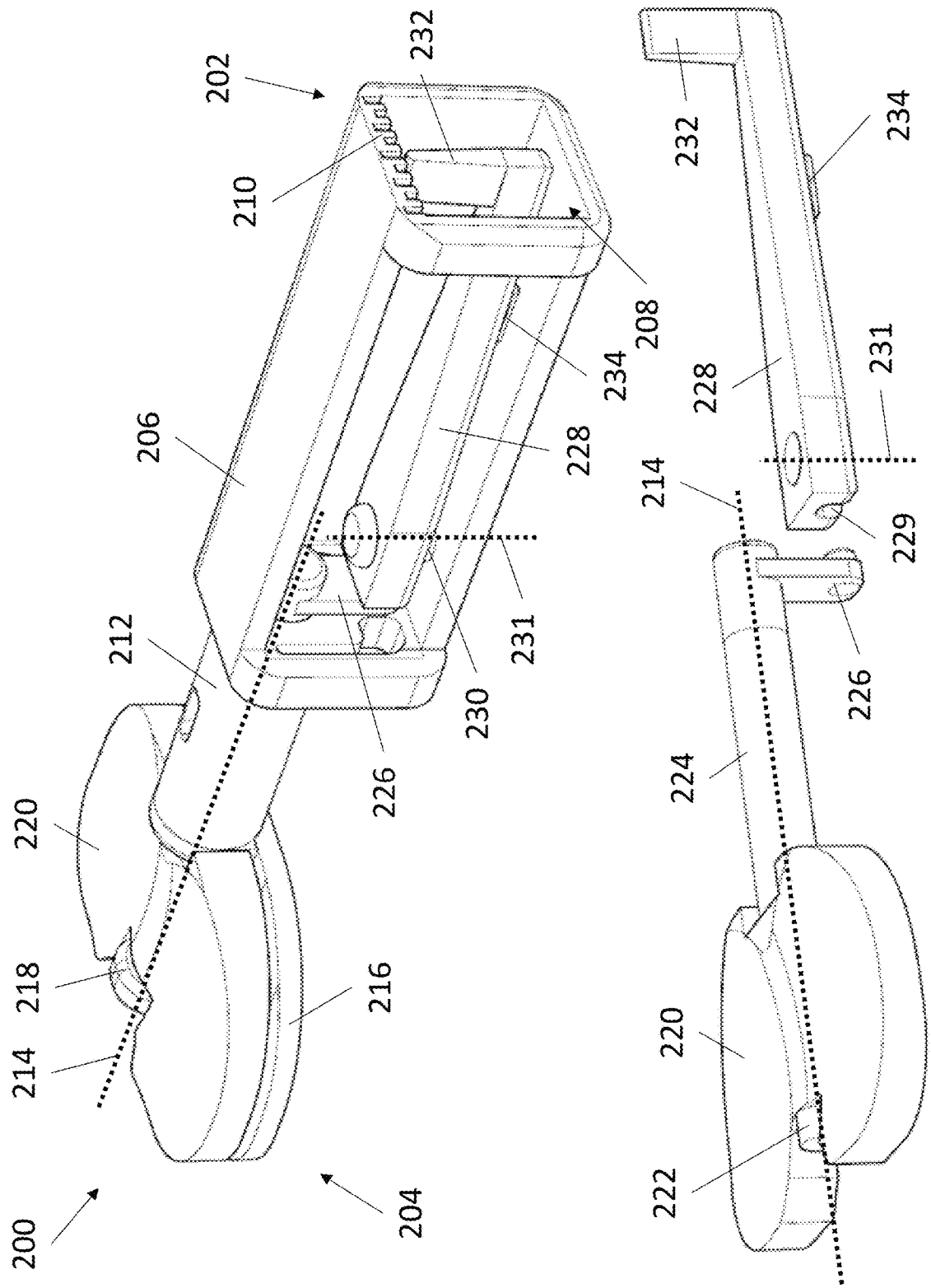
FIG. 9 depicts a partial cutaway view (top) and the internal components (bottom) of another exemplary balancer device.

Referring now to FIG. 9, an exemplary balancer device 200 is depicted. Balancer device 200 comprises a housing 206 with an anterior end 202 and a posterior end 204. Housing 206 comprises a window 208 at its anterior end 202 sized to fit a pointer or gauge 232. Housing 206 may further comprise a scale 210 positioned at its anterior end 202 that provides a graded measure of any suitable unit adjacent to window 208. For example, the scale can include at least one of force units, distance units, angle degrees, or unitless markings. Axle casing 212 extends posteriorly from posterior end 204 of housing 206 and connects at its posterior end to balancer plate 216. Axle casing 212 comprises a lumen extending from housing 206 to an open end adjacent to balancer plate 216. Balancer plate 216 can have any suitable shape, such as a substantially planar shape sized to fit within a joint space between two connected bones. Balancer plate 216 has an upper surface that interfaces with the lower surface of upper plate 220, such that a flat upper surface of balancer plate 216 fits with a flat lower surface of upper plate 220, and a curved upper surface of balancer plate 216 fits with a curved lower surface of upper plate 220. In some embodiments, balancer plate 216 has a flat lower surface. In other embodiments, balancer plate 216 has a contoured lower surface having a shape that fits in a joint space, such as a shape that fits with the condyles of a tibia in a knee joint. Balancer plate 216 includes axle slot 218 positioned opposite from the open end of axle casing 212 and aligned with the lumen of axle casing 212.

Upper plate 220 rests on the upper surface of balancer plate 216 and is connected to the posterior end of axle 224. Axle 224, aligned along axis 214, extends anteriorly through the lumen of axle casing 212 into housing 206. Upper plate 220 comprises axle tip 222 positioned opposite from axle 224 and aligned with axis 214. Upper plate 220 can have any suitable shape, such as a substantially planar shape sized to fit within a joint space between two connected bones. In some embodiments, upper plate 220 has a flat upper surface. In other embodiments, upper plate 220 has a contoured or concave upper surface having a shape that fits in a joint space, such as a shape that fits with the condyles of a femur in a knee joint. In some embodiments, the lower surface of upper plate 220 has springs positioned opposite from each other to the left and to the right of axle 224. The springs can be any suitable spring, such as a coil spring, a conical spring, a wave spring, a leaf spring, and the like. In some embodiments, the lower surface of upper plate 220 has a support formed by two downward sloping surfaces meeting at a middle edge resting against the top surface of balancer plate 216. In various embodiments, the lower surface of upper plate 220 and the upper surface of balancer plate 216 are maintained in parallel alignment at rest with a gap height in between. Upper plate 220 and balancer plate 216 can be separated by any suitable height, such as a height between about 1 and 5 mm or between about 1 and 3 mm. In some embodiments, the height between upper plate 220 and balancer plate 216 is 2.5 mm.

Balancer device 200 further comprises an elongate beam 228 having notch 229 at its posterior end 204 and pointer or gauge 232 positioned at its anterior end 202. Beam 228 is secured to the interior of housing 206 at pin 230 and is rotatable about pin 230 along pin axis 231. In some embodiments, pin 230 is movable along housing 206 and fits within an elongate slot within beam 228, enabling pin 230 to adjust the magnification of movement between the posterior end 204 of beam 228 and pointer or gauge 232. Axle 224 comprises table 226 at its anterior end 202 that seats within notch 229 of beam 228. In some embodiments, beam 228 further comprises spacer 234 to maintain the alignment between beam 228 and tab 226 of axle 224. Balancer device 200 is thereby able to provide a reading of the relative difference in force between the lateral and medial sides of a joint by translating displacement of upper plate 220 into a proportional movement of pointer or gauge 232. The displacement can be an angular displacement, a rotation, or a vertical displacement.

While joints attached to a body as a point of reference can have medial and lateral sides, for the sake of describing the function of balancer device 200 in an example, a hypothetical joint being measured by balancer device 200 has a left and a right side relative to the orientation of the device in FIG. 9. An imbalance in a hypothetical joint leads to a relative difference in force that is greater on the right side, which depresses the right side of upper plate 220 and causes axle 224 to rotate in a clockwise direction along axis 214, such as up to 5 degrees or up to 2.5 degrees. The rotation of axle 224 in a clockwise direction pivots tab 226 in a clockwise direction to the left, which pushes notch 229 and the posterior end 204 of beam 228 laterally to the left. Beam 228 rotates about pin axis 231, causing its anterior end 202 and pointer or gauge 232 to move laterally to the right. Movement in pointer or gauge 232 is thereby representative of a magnified magnitude of the movement of upper plate 220.

Figure 10:
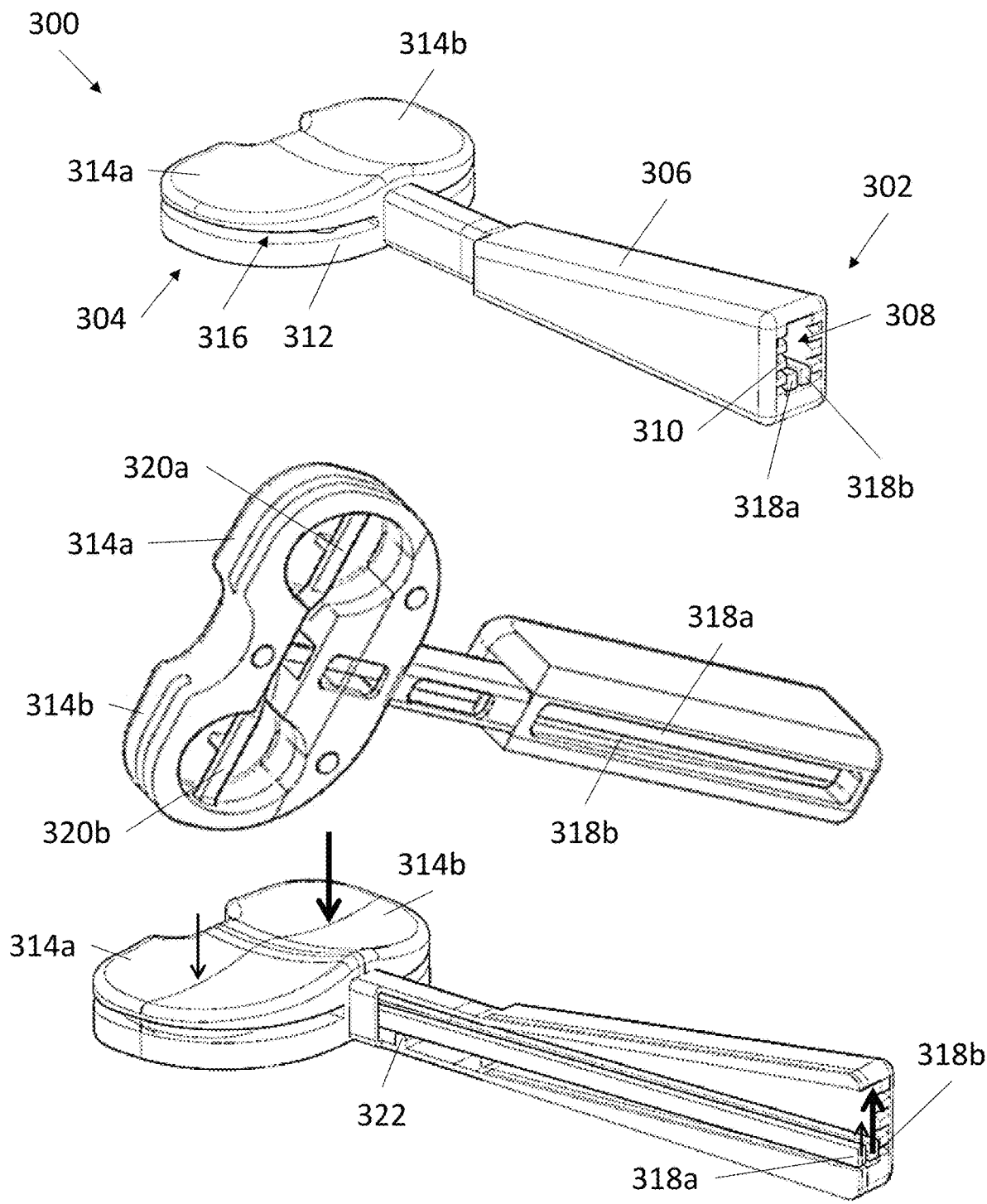
FIG. 10 depicts a perspective view (top), an underside view (middle), and a partial cutaway view (bottom) of another exemplary balancer device.

Referring now to FIG. 10, an exemplary balancer device 300 is depicted. Balancer device 300 comprises a housing 306 with an anterior end 302 and a posterior end 304. Housing 306 comprises a window 308 at its anterior end 302 wherein the anterior ends of long beam 318a and long beam 318b are visible. Housing 306 may further comprise a scale 310 positioned at its anterior end 302 that provides a graded measure of any suitable unit adjacent to window 308. For example, the scale can include at least one of force units, distance units, angle degrees, or unitless markings. Housing 306 connects at its posterior end 304 to lower plate 312, upper plate 314a, and upper plate 314b. Lower plate 312 can have any suitable shape, such as a substantially planar shape sized to fit within a joint space between two connected bones. Lower plate 312 can have a substantially flat lower surface to fit a flat surface of a resected joint or a contoured lower surface having a shape that fits in a joint space, such as a shape that fits with the condyles of a tibia in a knee joint. Upper plate 314a and upper plate 314b can each have any suitable shape, such as a substantially planar shape sized to fit within a joint space between two connected bones. In some embodiments, upper plate 314a and upper plate 314b each has a flat upper surface. In other embodiments, upper plate 314a and upper plate 314b each has a contoured or concave upper surface having a shape that fits in a joint space, such as a shape that fits with the condyles of a femur in a knee joint. Upper plate 314a and upper plate 314b are cantilevered over lower plate 312 and are maintained in parallel alignment by gap 316. Gap 316 can have any suitable height, such as a height between about 1 and 5 mm or between about 1 and 3 mm. In some embodiments, the height of gap 316 is 2.5 mm.

Balancer device 300 further comprises long beam 318a adjacent to long beam 318b, each positioned within the hollow interior of housing 306. Long beam 318a and long beam 318b each rest on fulcrum 322 positioned on the interior of housing 306. In some embodiments, fulcrum 322 is movable along housing 306 to adjust the magnification of movement between the posterior end 304 and the anterior end 302 of long beam 318a and long beam 318b. Long beam 318a and long beam 318b are each connected to short beam 320a and short beam 320b, respectively, at their posterior ends 304. Short beam 320a and short beam 320b are each positioned underneath upper plate 314a and upper plate 314b, respectively. Balancer device 300 is thereby able to provide a reading of the relative amount of force applied on the lateral and medial sides of a joint by translating displacement of upper plate 314a and upper plate 314b into a proportional movement of the anterior ends 302 of long beam 318a and long beam 318b.

While joints attached to a body as a point of reference can have medial and lateral sides, for the sake of describing the function of balancer device 300 in an example, a hypothetical joint being measured by balancer device 300 has a left and a right side relative to the orientation of the device in FIG. 10 (bottom). A hypothetical joint applies forces to upper plate 314a and upper plate 314b (which in this case is greater on the right side and lesser on the left side), which displaces upper plate 314b and short beam 320b in a greater inferior direction than upper plate 314a and short beam 320a. The inferior displacement of short beam 320a and short beam 320b also displaces the posterior ends 304 of long beam 318a and long beam 318b in an inferior direction, respectively, causing the anterior ends 302 of long beam 318a and long beam 318b to be displaced in a superior direction due to fulcrum 322. The greater inferior displacement of short beam 320b is translated to a proportionally greater superior displacement of the anterior end 302 of long beam 318b, and the lesser inferior displacement of short beam 320a is translated to a proportionally lesser superior displacement of the anterior end 302 of long beam 318a. Movement in the anterior ends 302 of long beam 318a and long beam 318b is thereby representative of a magnified magnitude of the movement of upper plate 314a and upper plate 314b, respectively.

Figure 11:
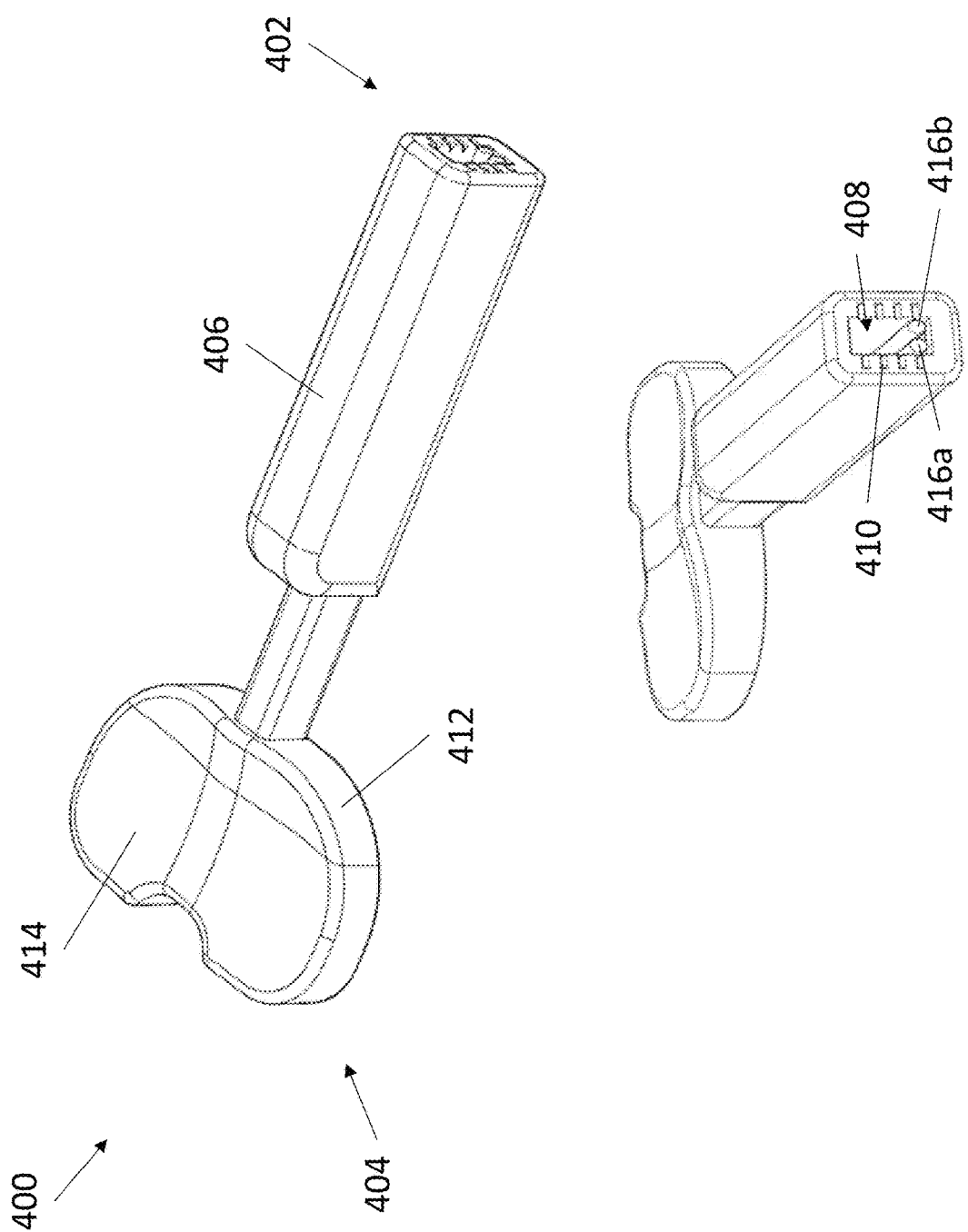
FIG. 11 depicts a perspective view (top) and a proximal view (bottom) of another exemplary balancer device.

Referring now to FIG. 11, an exemplary balancer device 400 is depicted. Balancer device 400 is similar to balancer device 300 in many respects, including a similar housing 406 having an anterior end 402 and a posterior end 404, a window 408, a scale 410, and long beam 416a and long beam 416b each resting on a fulcrum (not visible) and connected at their posterior ends 404 to short beams (not visible). Balancer 400 further employs a lower plate 412 that is covered by membrane 414. Balancer device 400 functions similarly to balancer device 300, wherein displacement of the left or right side of membrane 414 corresponds to an inferior displacement of a corresponding short beam and a superior displacement of the anterior end 402 of a corresponding long beam 416a and/or long beam 416b.

Figure 12:
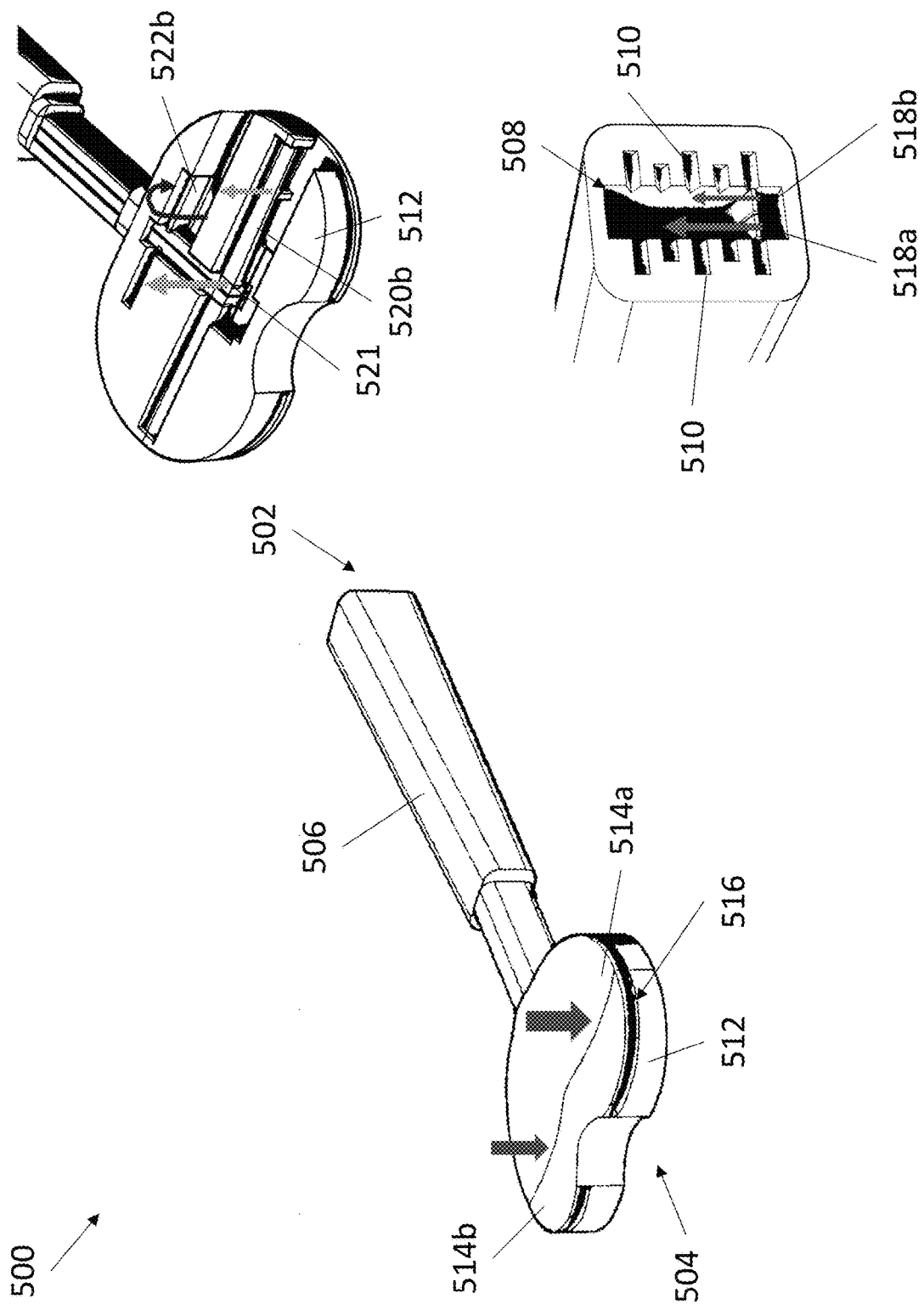
FIG. 12 depicts a perspective view (left), a partial cutaway view (top right), and a rear view (bottom right) of another exemplary balancer device.
Figure 13:
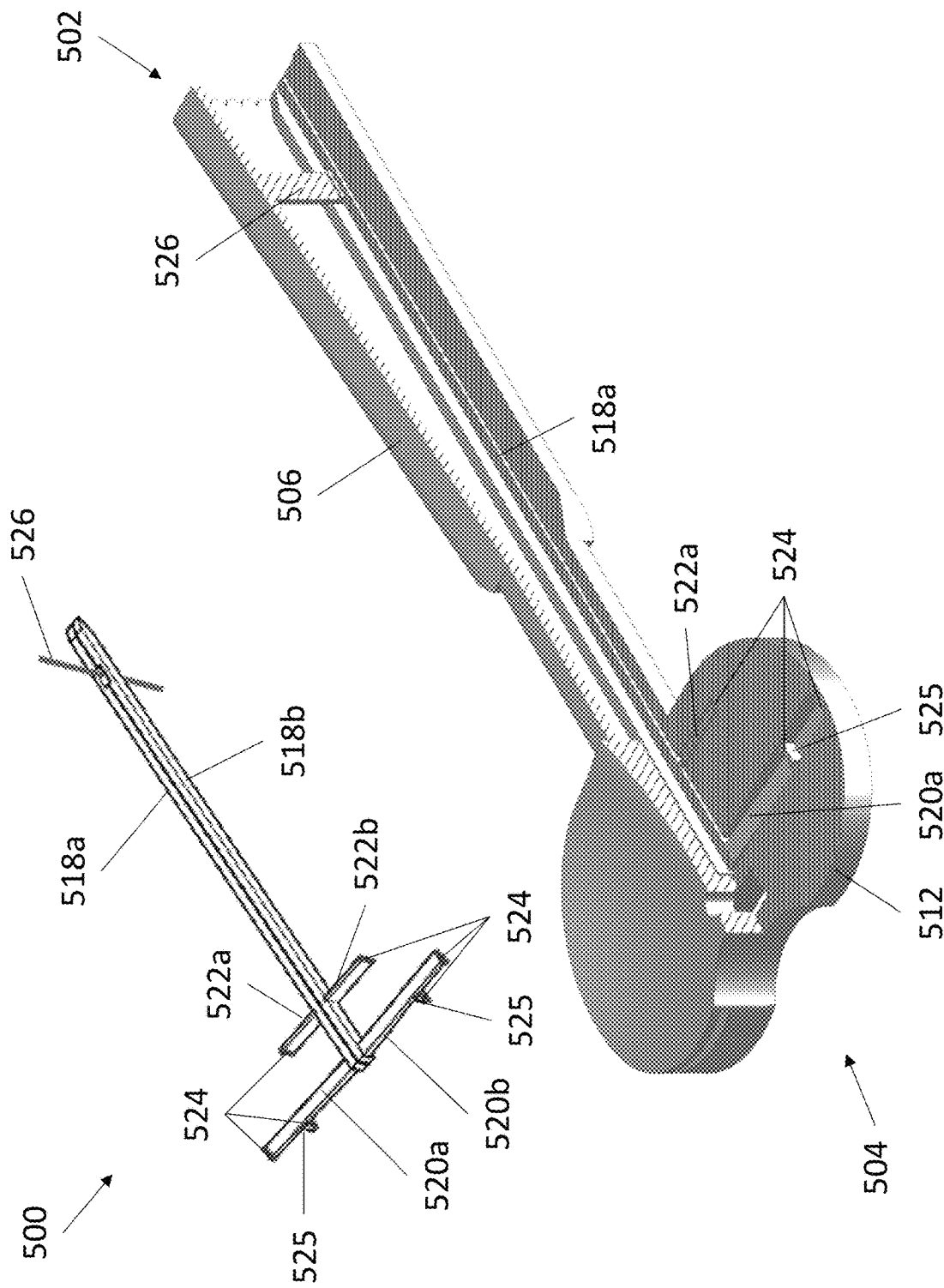
FIG. 13 depicts a perspective view of the internal beams in isolation (top left) and a partial cutaway view (bottom right) of the balancer device in FIG. 12.

Referring now to FIG. 12 and FIG. 13, an exemplary balancer device 500 is depicted. Balancer device 500 is similar to balancer device 300 in many respects, including a similar housing 506 having an anterior end 502 and a posterior end 504, lower plate 512 positioned inferior to upper plate 514a and upper plate 514b separated by a gap 516, a window 508, a scale 510, and long beam 516a and long beam 516b connected at their posterior ends 504 to short beam 520a and short beam 520b, respectively. Likewise, lower plate 512 can have any suitable shape, such as a substantially planar shape sized to fit within a joint space between two connected bones. Lower plate 512 can have a substantially flat lower surface to fit a flat surface of a resected joint or a contoured lower surface having a shape that fits in a joint space, such as a shape that fits with the condyles of a tibia in a knee joint. Upper plate 514a and upper plate 514b can each have any suitable shape, such as a substantially planar shape sized to fit within a joint space between two connected bones. In some embodiments, upper plate 514a and upper plate 514b each has a flat upper surface. In other embodiments, upper plate 514a and upper plate 514b each has a contoured or concave upper surface having a shape that fits in a joint space, such as a shape that fits with the condyles of a femur in a knee joint. Upper plate 514a and upper plate 514b are cantilevered over lower plate 512 and are maintained in parallel alignment by gap 516. Gap 516 can have any suitable height, such as a height between about 1 and 5 mm or between about 1 and 3 mm. In some embodiments, the height of gap 516 is 2.5 mm.

Referring now to FIG. 13, the internal beams of balancer device 500 are now described. The top left image of FIG. 13 depicts a posterior view of the internal beams in isolation, while the bottom right image of FIG. 13 depicts a partial cutaway view of the internal beams within balancer device 500. Short beam 520a and short beam 520b each extend laterally from an interior lateral surface of lower plate 512 at an attachment point 524, and are each further attached to a respective upper plate 514a and upper plate 514b by a short vertical beam 525. Fulcrum beam 522a and fulcrum beam 522b each also extend laterally from an interior lateral surface of lower plate 512 at an attachment point 524 that is posterior to short beam 520a and short beam 520b, respectively. Long beam 518a and long beam 518b are each connected to a respective short beam 520a and fulcrum beam 522a and short beam 520b and fulcrum beam 522b. Accordingly, long beam 518a and long beam 518b are suspended within housing 506 by connecting only to a respective short beam and fulcrum beam.

In some embodiments, balancer device 500 comprises a single piece construction, such that every component on balancer device 500 described herein is part of a continuous piece of a single material. In other words, short beam 520a and short beam 520b can be described as the material of housing 506 extending into the interior of lower plate 512 from the respective attachment points 524; fulcrum beam 522a and fulcrum beam 522b can also be described as the material of housing 506 extending into the interior of lower plate 512 from the respective attachment points 524; and long beam 518a and long beam 518b can be described as the material of housing 506 extending through each of the short beams and fulcrum beams.

Balancer device 300 is thereby able to provide a reading of the relative amount of force applied on the lateral and medial sides of a joint by translating displacement of upper plate 514a and upper plate 514b into a proportional movement of the anterior ends 502 of long beam 518a and long beam 518b. In some embodiments, balancer device 500 further comprises a vertical guide beam 526 positioned within the interior of housing 506, such that long beam 518a and long beam 518b each comprises a cutout to fit around guide beam 526. Guide beam 526 enhances the stability of long beam 518a and long beam 518b when they are vertically displaced.

Referring back to FIG. 12, the displacement translation is now described. While joints attached to a body as a point of reference can have medial and lateral sides, for the sake of describing the function of balancer device 500 in an example, a hypothetical joint being measured by balancer device 500 has a left and a right side relative to the orientation of the device in FIG. 12 (left). A hypothetical joint applies forces to upper plate 514a and upper plate 514b (which in this case is greater on the right side and lesser on the left side), which displaces upper plate 514a and short beam 520a in a greater inferior direction than upper plate 514b and short beam 520b. The inferior displacement of short beam 520a and short beam 520b also displaces the posterior ends 504 of long beam 518a and long beam 518b in an inferior direction, respectively. Due to the connection between each long beam and a respective fulcrum beam, long beam 518a and long beam 518b each rotates about fulcrum beam 522a and 522b, respectively (visible in FIG. 12, top right), causing the anterior ends 502 of long beam 518a and long beam 518b to be displaced in a superior direction (visible in FIG. 12, bottom right). The greater inferior displacement of short beam 520a is translated to a proportionally greater superior displacement of the anterior end 502 of long beam 518a, and the lesser inferior displacement of short beam 520b is translated to a proportionally lesser superior displacement of the anterior end 502 of long beam 518b. Movement in the anterior ends 502 of long beam 518a and long beam 518b is thereby representative of a magnified magnitude of the movement of upper plate 514a and upper plate 514b, respectively.

While exemplary balancer devices of the present invention are described above, the balancer devices are nonetheless amenable to any suitable modification to augment their function. In various embodiments, the dimensions of the plates of the balancer devices described elsewhere herein are amenable to adjustment. For example, in certain embodiments, the plates can receive one or more additional spacer plates having substantially similar planar shapes with different heights, such that the one or more additional spacer plates can be attached to the upper surface of the upper plates and/or the lower surfaces of the lower balancer plates to increase the height of each plate. In other embodiments, the plates can be removable and replaceable with plates having different planar shapes or different heights. In various embodiments, the one or more additional spacer plates and the replaceable plates can be used to adjust the contours of the plates to improve the fit between the balancer devices and a joint of interest. In various embodiments, the upper surfaces of the upper plates are shallow and concave, such that the femoral component of any condylar replacement artificial knee can be located at two separate points, with only small constraint.

In various embodiments, the several components of the assorted balancer devices can be combined and rearranged without altering their function to accommodate different orientations and configurations. For example, exemplary balancer devices described herein have vertically oriented handles, but it should be understood that embodiments having horizontally oriented handles, handles in line with the axles and axle casings, and variously angled and dimensioned handles are contemplated.

The components of the balancer devices of the present invention can be made using any suitable method known in the art. The method of making may vary depending on the materials used. For example, components substantially comprising a metal may be milled from a larger block of metal or may be cast from molten metal. Likewise, components substantially comprising a plastic or polymer may be milled from a larger block, cast, or injection molded. In some embodiments, the components may be made using 3D printing or other additive manufacturing techniques commonly used in the art. 3D printing enables the entirety of the device to be printed in a single session with a brief post-processing treatment that removes sacrificial support structures between movable parts. In some embodiments, the materials can withstand commonly used sterilization techniques, enabling the devices to be reusable. In other embodiments, inexpensive methods permit the devices to be single-use and disposable.

Method of Use

Figure 14:
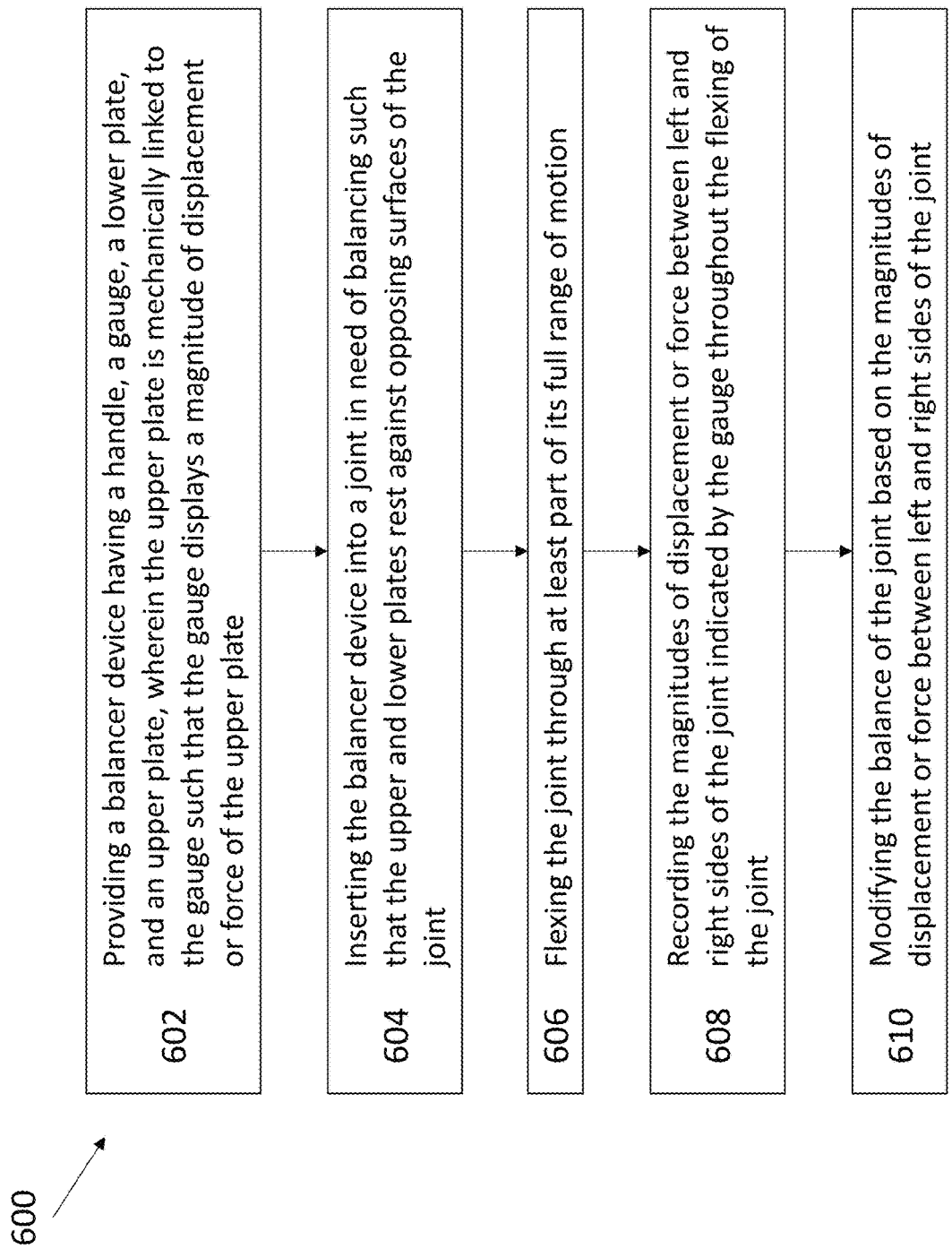
FIG. 14 is a flowchart depicting an exemplary method of balancing a joint using a balancer device.

The present invention also includes methods of using the balancer devices described herein to balance a joint. Referring now to FIG. 14, an exemplary method 600 of balancing a joint is depicted. Method 600 begins with step 602, wherein a balancer device having a handle, a gauge, a lower plate, and an upper plate, wherein the upper plate is mechanically linked to the gauge such that the gauge displays a magnitude of displacement or force of the upper plate is provided. In step 604, the balancer device is inserted into a joint in need of balancing such that the upper and lower plates rest against opposing surfaces of the joint. In step 606, the joint is flexed through at least part of its full range of motion. In step 608, the magnitudes of displacement or force between left and right sides of the joint indicated by the gauge are recorded throughout the flexing of the joint. In step 610, the balance of the joint is modified based on the magnitudes of displacement or force between left and right sides of the joint.

The joint can be any suitable joint, including but not limited to knee joints and elbow joints. The opposing surfaces of the joint can thereby be opposing bone surfaces of the joint, such as the femoral condyles and the tibial condyles of the knee. In certain embodiments, the balancer devices are useful in balancing joint replacements. In some embodiments, the balancer devices are useful in balancing total knee replacements. The opposing surfaces of the joint can thereby be opposing implant surfaces of the joint replacement, such as the trial femoral condyles and the trial tibial plateau of a replacement knee, as well as any opposing bone surfaces of the joint that contact the implant surfaces. A joint in need of balancing can register displacements or forces that are either too great or too small. The balance of the joint can be modified in any suitable manner. For example, the opposing surfaces may be trimmed or raised to balance any relative differences in force between the left and right sides of the joint. The joint can also be balanced by performing ligament releases or making small angular changes to the femoral or tibial cut surfaces. In certain joint replacements, the joining of the opposing surfaces can be modified by adjusting a spacer component that fits between the opposing surfaces. The gauge readings can indicate the magnitudes or ratios of displacement or force on the left or right side of the joint. In some embodiments, the displacement or force on the balancer device may be too small to be perceptible, such as in a case where contact forces between the joint and the balancer device may not be enough. Contact forces can be increased by adding one or more additional spacer plates to the upper surfaces of the upper plates and/or lower surfaces of the lower balancer plates to increase the height of each plate.

In some embodiments, steps 602 through step 610 are performed in the order recited. In some embodiments, step 604 through step 608 may be repeated to verify that the modification performed in step 610 correctly balanced the joint. If the repeated step 608 indicates that the magnitudes of displacement or force are satisfactorily balanced, then the joint is substantially balanced. If the repeated step 608 indicates that unsatisfactorily high magnitudes or low magnitudes of displacement or force are still present, step 610 may be repeated. In some embodiments, step 604 through step 610 may be repeated until the magnitudes of displacement or force are satisfactorily balanced.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A joint balancer device, comprising:
    a handle having a gauge;
    a lower plate attached to the handle; and
    an upper plate aligned in parallel with the lower plate by a gap space, wherein the upper plate is displaceable relative to the lower plate;
    wherein the upper plate is connected by a mechanical link to the gauge, and wherein the mechanical link magnifies displacement of the upper plate such that the gauge displays the magnified displacement, wherein the mechanical link comprises:
    a first and a second long beam adjacently positioned within a hollow interior of the handle, each long beam having an anterior end as a pointer of the gauge;
    a first short beam extending from an interior of the lower plate in a lateral direction underneath a left side of the upper plate such that the first short beam attaches to a posterior end of the first long beam, wherein the first short beam is further connected to the upper plate by a short vertical beam;
    a second short beam extending from an interior of the lower plate in a lateral direction underneath a right side of the upper plate such that the second short beam attaches to a posterior end of the second long beam, wherein the second short beam is further connected to the upper plate by a short vertical beam;
    a first fulcrum beam extending from an interior of the lower plate in a lateral direction underneath a left side of the upper plate, the first fulcrum beam positioned anterior to the first short beam such that the first fulcrum beam attaches to the first long beam at a position anterior to the first short beam; and
    a second fulcrum beam extending from an interior of the lower plate in a lateral direction underneath a right side of the upper plate, the second fulcrum beam positioned anterior to the second short beam such that the second fulcrum beam attaches to the second long beam at a position anterior to the second short beam.

2. The device of claim 1, wherein an inferior displacement of a side of the upper plate inferiorly displaces the respective short beam underneath the side of the upper plate, such that the respective connected long beam is actuated about the respective fulcrum beam to shift the pointer of the gauge in a superior direction.

3. The device of claim 2, wherein the upper plate comprises flexible membranes above the first and second short beams.

4. The device of claim 1, wherein the upper plate has an upper surface contoured to fit a femur's condyles or a trial femoral component of a total knee replacement, and the lower plate has a lower surface contoured to fit a resected surface of a tibia in a total knee replacement.

5. The device of claim 1, wherein the upper plate and the lower plate are separated by a substantially parallel distance between about 1 and 3 mm.

6. The device of claim 5, wherein the upper plate is cantilevered over the lower plate by the distance.

7. The device of claim 5, wherein the distance is maintained in a neutral state by one or more springs positioned between the upper plate and the lower plate, the one or more springs selected from the group consisting of: coil springs, conical springs, wave springs, and leaf springs.

8. The device of claim 1, wherein the gauge includes a scale having at least one of force units, distance units, angle degrees, or unitless markings.

9. The device of claim 1, wherein the device is configured to measure a relative difference in force between a lateral side and a medial side of a joint.

10. A method of balancing a joint, comprising the steps of:
    providing the balancer device of claim 1;
    inserting the balancer device into a joint in need of balancing such that the upper and lower plates rest against opposing surfaces of the joint;
    flexing the joint through at least part of its full range of motion;
    recording magnitudes of displacement or force between left and right sides of the joint indicated by the gauge throughout the flexing of the joint;
    removing the balancer device from the joint; and
    modifying a balance of the joint based on the magnitudes of displacement or force between left and right sides of the joint.

11. The method of claim 10, wherein the joint is a knee joint or an elbow joint.

12. The method of claim 10, wherein the opposing joint surfaces are opposing bone surfaces, opposing implant surfaces, or combinations thereof.

13. The method of claim 10, wherein the balance of the joint is modified by trimming the opposing surfaces, raising the opposing surfaces, adjusting a spacer component between the opposing surfaces, or combinations thereof.

14. The method of claim 10, wherein contact forces are increased between the joint and the balancer device by adding one or more additional spacer plates to the upper plate and/or lower plate.

* * * * *